US011299165B2

(12) United States Patent
Takahashi

(10) Patent No.: US 11,299,165 B2
(45) Date of Patent: Apr. 12, 2022

(54) EVALUATION DEVICE AND EVALUATION METHOD

(71) Applicant: SONY CORPORATION, Tokyo (JP)

(72) Inventor: Shuichi Takahashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/254,359

(22) PCT Filed: Apr. 15, 2019

(86) PCT No.: PCT/JP2019/016182
§ 371 (c)(1),
(2) Date: Dec. 21, 2020

(87) PCT Pub. No.: WO2020/003697
PCT Pub. Date: Jan. 2, 2020

(65) Prior Publication Data
US 2021/0269043 A1 Sep. 2, 2021

(30) Foreign Application Priority Data

Jun. 27, 2018 (JP) .............................. JP2018-122301

(51) Int. Cl.
B60W 40/08 (2012.01)
A61B 5/369 (2021.01)
A61B 5/18 (2006.01)
(52) U.S. Cl.
CPC .............. *B60W 40/08* (2013.01); *A61B 5/18* (2013.01); *A61B 5/369* (2021.01);
(Continued)

(58) Field of Classification Search
None
See application file for complete search history.

(56) References Cited

U.S. PATENT DOCUMENTS 6,167,298 A * 12/2000 Levin .................. A61B 5/6803
600/545
2011/0288424 A1* 11/2011 Kanai .................. A61B 5/369
600/500

FOREIGN PATENT DOCUMENTS

JP 2006-280513 A 10/2006
JP 2007-171154 A 7/2007
(Continued)

OTHER PUBLICATIONS

International Search Report and Written Opinion of PCT Application No. PCT/JP2019/016182, dated Jun. 4, 2019, 08 pages of ISRWO.

*Primary Examiner* — Thomas S McCormack
(74) *Attorney, Agent, or Firm* — Chip Law Group

(57) ABSTRACT

To enhance safety in vehicle operation. An evaluation device according to the present technology includes a communication unit capable of communicating with a vehicle, and a control unit that performs an evaluation of a state related to sensing of danger by a user on the basis of an electroencephalogram of the user detected by an electroencephalogram sensor, and causes the communication unit to transmit evaluation result information to the vehicle. That is, for example, on the basis of an electroencephalogram of a user such as a driver of a vehicle, evaluation of a state related to sensing of danger such as whether or not the user has sensed a danger is performed, and evaluation result information is transmitted to the vehicle side.

9 Claims, 11 Drawing Sheets

(52) U.S. Cl.
CPC . *B60W 2040/0818* (2013.01); *B60W 2540/22* (2013.01); *B60W 2540/229* (2020.02)

(56) References Cited

FOREIGN PATENT DOCUMENTS

| | | |
|---|---|---|
| JP | 2014-089557 A | 5/2014 |
| JP | 2017-037359 A | 2/2017 |
| JP | 2017-068761 A | 4/2017 |
| WO | 2014/024606 A1 | 2/2014 |

\* cited by examiner

FIG. 8

| DATE AND TIME | POSITION | ELECTROENCEPHALOGRAM DATA | AVOIDANCE BEHAVIOR | VEHICLE STATE | COLLIDED OR NOT |
|---|---|---|---|---|---|
| ×××/○○/△△ | P00001 | DATA A | SUDDEN BRAKING AND SUDDEN STEERING | VEHICLE SPEED = 50Km/h WITHOUT PEDESTRIAN OR ANOTHER CAR | NOT COLLIDED |
| ×××/△△/○× | P0008 | DATA B | | VEHICLE SPEED = 70Km/h WITHOUT PEDESTRIAN, WITH ANOTHER CAR | COLLIDED |
| ... | ... | ... | ... | ... | ... |
| ×××○/△△/○□ | P0001 | DATA X | SUDDEN BRAKING | VEHICLE SPEED = 40Km/h WITHOUT PEDESTRIAN OR ANOTHER CAR | NOT COLLIDED |

FIG. 9

| POSITION | REPRESENTATIVE ELECTROENCEPHALOGRAM DATA |
|---|---|
| P00001 | DATA a |
| P0002 | DATA b |
| ⋮ | ⋮ |
| Pxxxx | DATA x |

| POSITION | REPRESENTATIVE ELECTROENCEPHALOGRAM DATA | RECOMMENDED AVOIDANCE BEHAVIOR |
|---|---|---|
| P00001 | DATA a | AT LOW SPEED = SUDDEN BRAKING<br>AT HIGH SPEED = SUDDEN BRAKING AND SUDDEN STEERING |
| P0002 | DATA b | SUDDEN BRAKING |
| ⋮ | ⋮ | ⋮ |
| Pxxxx | DATA x | NONE |

EVALUATION DEVICE AND EVALUATION METHOD

CROSS REFERENCE TO RELATED APPLICATIONS

This application is a U.S. National Phase of International Patent Application No. PCT/JP2019/016182 filed on Apr. 15, 2019, which claims priority benefit of Japanese Patent Application No. JP 2018-122301 filed in the Japan Patent Office on Jun. 27, 2018. Each of the above-referenced applications is hereby incorporated herein by reference in its entirety.

TECHNICAL FIELD

The present technology relates to an evaluation device and a method for evaluating a state related to sensing of danger by a user who is, for example, a driver of a vehicle.

BACKGROUND ART

For example, as disclosed in Patent Documents 1 to 3 described below, it is conceivable to monitor a psychological condition or a health condition of a driver of a vehicle by biological information such as pulse, heartbeat, or the like for use in safety control.

When an abnormality is found in the driver's condition, it is conceivable to alert an occupant of the vehicle or surrounding vehicles, or to automatically reduce speed.

CITATION LIST

Patent Document

Patent Document 1: Japanese Patent Application Laid-Open No. 2006-280513
Patent Document 2: Japanese Patent Application Laid-Open No. 2014-89557
Patent Document 3: WO 2014-24606 A

SUMMARY OF THE INVENTION

Problems to be Solved by the Invention

It is an object of the present technology to enhance safety in vehicle operation.

Solutions to Problems

An evaluation device according to the present technology includes a communication unit capable of communicating with a vehicle, and a control unit that performs an evaluation of a state related to sensing of danger by a user on the basis of an electroencephalogram of the user detected by an electroencephalogram sensor, and causes the communication unit to transmit evaluation result information to the vehicle.

That is, for example, on the basis of an electroencephalogram of a user such as a driver of a vehicle, evaluation of a state related to sensing of danger such as whether or not the user has sensed a danger is performed, and evaluation result information is transmitted to the vehicle side.

In the evaluation device according to the present technology described above, it is desirable that the control unit perform the evaluation of a state related to sensing of danger on the basis of at least one of a magnitude of amplitude of a beta wave in an electroencephalogram, a power level of the beta wave, or a phase of the beta wave.

When a danger approaches and tension rises, an amplitude and power of a beta wave change. Furthermore, when beta waves detected at a plurality of positions in a brain are out of phase, there is a possibility that the evaluation of a state related to sensing of danger becomes less accurate. Thus, the state is evaluated in consideration of a magnitude of amplitude, a power level, and a phase of a beta wave.

In the evaluation device according to the present technology described above, it is desirable that the control unit perform the evaluation of a state related to sensing of danger on the basis of a relative comparison between a beta wave and a component other than the beta wave in an electroencephalogram.

That is, the evaluation of a state related to sensing of danger is performed on the basis of a relative comparison with a component other than the beta wave such as an alpha wave or a theta wave, not on the basis of the beta wave alone.

In the evaluation device according to the present technology described above, it is desirable that the control unit perform, when a current position is a position where an avoidance behavior has been taken in the past and an electroencephalogram immediately before the avoidance behavior has been recorded, the evaluation of a state related to sensing of danger on the basis of a result of matching between an electroencephalogram detected by the electroencephalogram sensor and the electroencephalogram immediately before the avoidance behavior.

This makes it possible to appropriately evaluate, on the basis of past records, a possibility that a user will take an avoidance behavior such as sudden braking or sudden steering in accordance with sensing of danger.

In the evaluation device according to the present technology described above, it is desirable that the control unit execute transmission processing for transmitting, to an external device, current position information, information regarding an electroencephalogram detected by the electroencephalogram sensor, and motion information detected by a motion sensor.

This makes it possible to build, outside the evaluation device, a database (table information) for managing information such as a place where a user has sensed a danger, an electroencephalogram at the time of sensing of danger, a content of an avoidance behavior taken in accordance with sensing of danger, and whether an accident has occurred (whether a collision has occurred).

In the evaluation device according to the present technology described above, it is desirable that the control unit execute the transmission processing in accordance with a result of the evaluation of a state related to sensing of danger.

This allows processing of transmitting information for risk analysis such as an electroencephalogram to an external device to be executed if it is evaluated that a user has sensed a danger, and not to be executed if it is evaluated that the user has not sensed a danger.

In the evaluation device according to the present technology described above, it is desirable that the control unit extract a feature amount of an electroencephalogram detected by the electroencephalogram sensor, and perform the transmission processing for transmitting information regarding the extracted feature amount.

With this arrangement, an amount of data can be reduced as compared with a case where an electroencephalogram signal itself detected by the electroencephalogram sensor is transmitted.

In the evaluation device according to the present technology described above, it is desirable that the control unit perform the transmission processing for transmitting vehicle information acquired from the vehicle via the communication unit.

This makes it possible to build, outside the evaluation device, a database for managing information indicating a vehicle state corresponding to the time of sensing of danger, in addition to information indicating a place where a user has sensed a danger, an avoidance behavior has been taken, or an accident has occurred.

In the evaluation device according to the present technology described above, it is desirable that the control unit cause the communication unit to transmit, to the vehicle, information regarding an avoidance behavior recorded in association with a current position on the basis of a result of the evaluation of a state related to sensing of danger.

This makes it possible to transmit, to the vehicle, information regarding an avoidance behavior recorded in association with the current position when it is evaluated that a user has sensed a danger.

Furthermore, an evaluation method according to the present technology includes evaluating a state related to sensing of danger by a user on the basis of an electroencephalogram of the user detected by an electroencephalogram sensor, and causing a communication unit capable of communicating with a vehicle to transmit evaluation result information to the vehicle.

Such an evaluation method also makes it possible to obtain an operation similar to that of the evaluation device according to the present technology described above.

Effects of the Invention

According to the present technology, it is possible to enhance safety in vehicle operation.

Note that the effects described here are not necessarily restrictive, and the effects of the invention may be any one of the effects described in the present disclosure.

BRIEF DESCRIPTION OF DRAWINGS

FIG. 8 illustrates an example of a data structure of an analysis table in the embodiment.

FIG. 9 illustrates an example of a data structure of an evaluation table in the embodiment.

MODE FOR CARRYING OUT THE INVENTION

An embodiment according to the present technology will be described below in the following order with reference to the accompanying drawings.

<1. Overview of driving support system>
[1-1. System overview]
[1-2. Configuration of evaluation device]
[1-3. Configuration of vehicle]
[1-4. Configuration of server device]
<2. Driving support method as embodiment>
<3. Processing procedure>
<4. Modifications of embodiment>
[4-1. First modification]
[4-2. Second modification]
[4-3. Other modifications]
<5. Summary of embodiment>
<6. Present technology>

1. Overview of Driving Support System 1-1. System Overview

Figure 1:
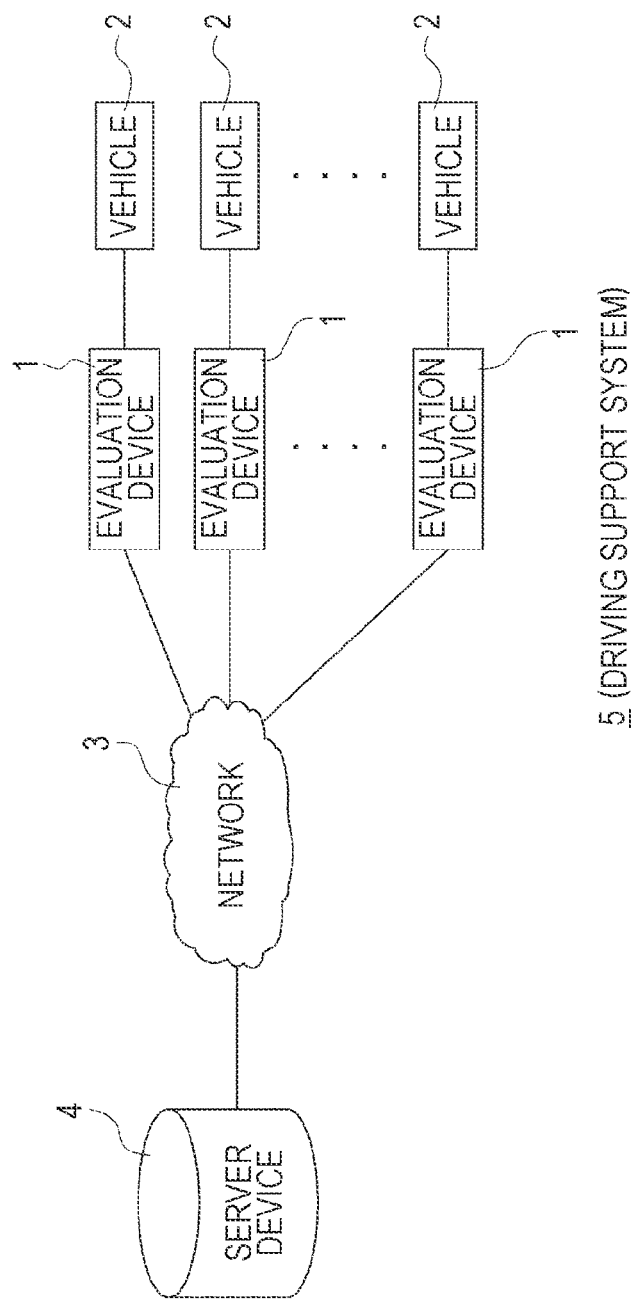
FIG. 1 is a diagram illustrating a configuration example of a driving support system including an evaluation device as an embodiment according to the present technology.

FIG. 1 illustrates a configuration example of a driving support system 5 including an evaluation device 1 as an embodiment according to the present technology.

The driving support system 5 includes a plurality of the evaluation devices 1, a plurality of vehicles 2, and a server device 4 that can communicate with each evaluation device 1 via a network 3. The network 3 is, for example, the Internet.

In the present example, the evaluation device 1 is a device worn by a user who is a driver of a vehicle 2, and can perform data communication with the vehicle 2.

The vehicle 2 can execute a control related to driving support such as automatic braking and automatic steering.

Figure 2:
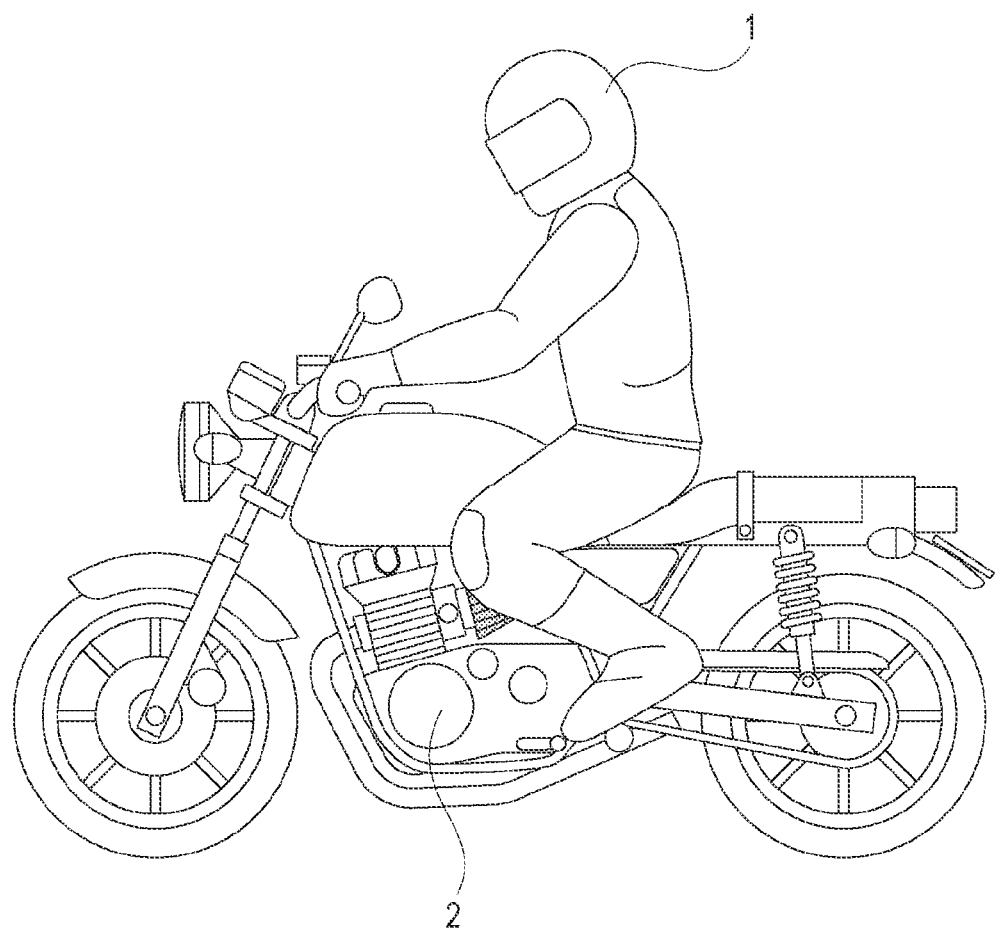
FIG. 2 is a diagram illustrating an external configuration example of the evaluation device and a vehicle as the embodiment.

FIG. 2 illustrates an external configuration example of the evaluation device 1 and the vehicle 2. In the present example, the vehicle 2 is a motorcycle, and the evaluation device 1 has, for example, a helmet-like shape.

As will be described later, the evaluation device 1 has a function of detecting a user's electroencephalogram. The evaluation device 1 also has a function of detecting a current position, a function of detecting a motion by an acceleration sensor or the like, and a function of acquiring vehicle information such as a vehicle speed from the vehicle 2.

Note that the evaluation device 1 is not limited to being worn by a user, but may be mounted on the vehicle 2. In that case, an electroencephalogram sensor 11, which will be described later, is externally attached to the evaluation device 1.

In the driving support system 5, on the basis of a result of detecting an electroencephalogram of a user who drives the vehicle 2, the evaluation device 1 evaluates a state related to sensing of danger by the user. Then, the evaluation device 1 transmits information indicating a result of the evaluation of the state related to sensing of danger to the corresponding vehicle 2 (that is, the vehicle 2 driven by the user wearing the evaluation device 1). With this arrangement, the vehicle 2 can reflect, in a driving support control, the result of the evaluation of the state related to sensing of danger by the user.

Furthermore, in the driving support system 5 of the present example, the evaluation device 1 performs, on the basis of the detected electroencephalogram, an evaluation as to whether or not the user has sensed a danger. When it is evaluated that a danger has been sensed, information indicating a situation in which the danger has been sensed is transmitted to the server device 4 via the network 3.

As the information transmitted at this time, which will be described later in detail, at least information regarding the detected electroencephalogram, information indicating a detected motion, and vehicle information acquired from the vehicle 2, together with current position information acquired at the time of sensing of danger, are transmitted to the server device 4.

With this arrangement, in the server device 4, it is possible to collect, from each evaluation device 1, a place where a user has perceived a danger, a motion performed when the user has perceived the danger (it can also be said as a behavior of the vehicle 2), and the vehicle information.

The information collected in this way can be used for analysis of the kind of place the user driving the vehicle 2 has perceived a danger, the kind of avoidance behavior the user has taken when the user has perceived the danger, and the like.

1-2. Configuration of Evaluation Device

Figure 3:
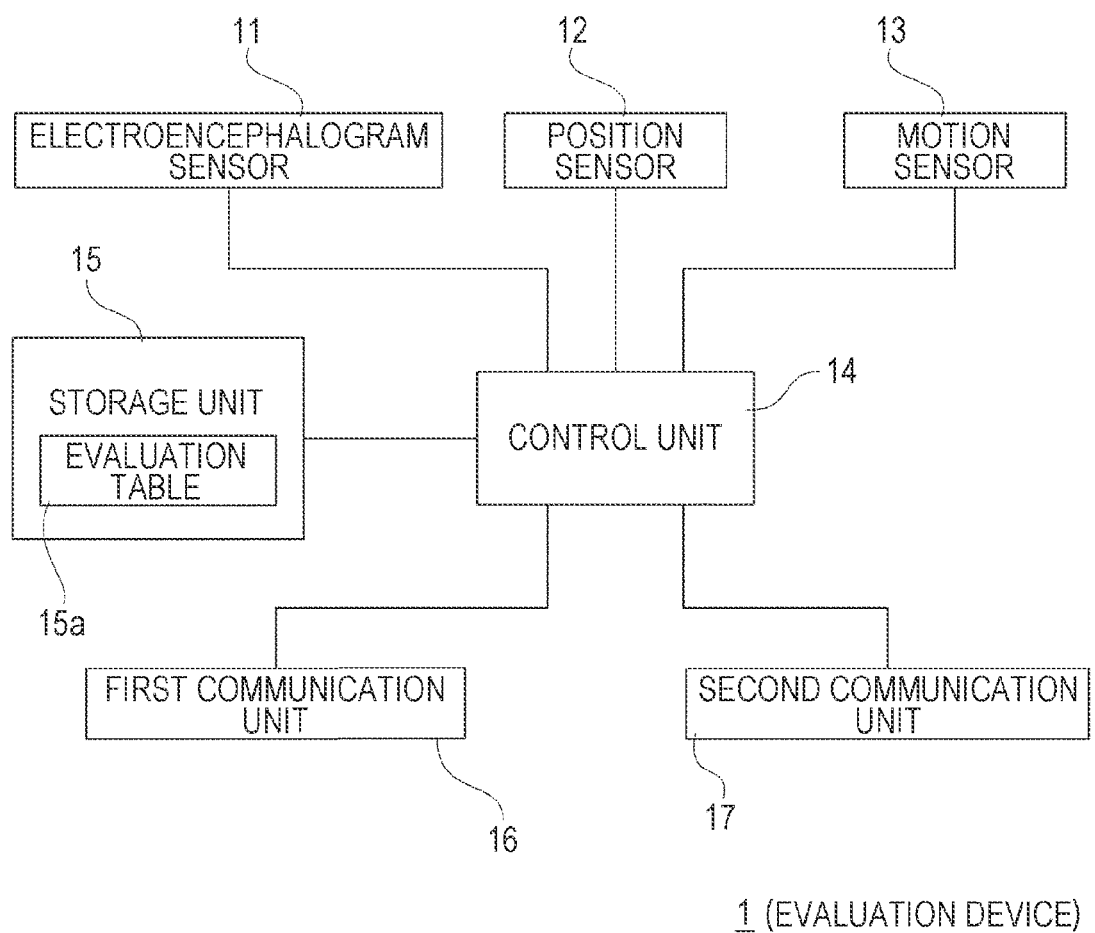
FIG. 3 is a diagram illustrating an internal configuration example of the evaluation device as the embodiment.

FIG. 3 is a diagram illustrating an internal configuration example of the evaluation device 1.

As illustrated, the evaluation device 1 includes the electroencephalogram sensor 11 that detects an electroencephalogram, a position sensor 12 that detects a position, a motion sensor 13 that detects a motion, a control unit 14 to which a detection signal from each of these sensors is input, a storage unit 15 that stores various types of information, and a first communication unit 16 and a second communication unit 17 for performing data communication with an external device.

The electroencephalogram sensor 11 has a plurality of electrodes in contact with a scalp of a user, and an electroencephalogram of the user is detected by the electrodes.

The position sensor 12 is, for example, a global navigation satellite system (GNSS) sensor such as a global positioning system (GPS) sensor, and detects a position.

The motion sensor 13 comprehensively represents sensors that detect a motion, such as a G-sensor (acceleration sensor), a gyro sensor (angular velocity sensor), and the like. In the present example, a G-sensor and a gyro sensor are provided as the motion sensor 13, and therefore motion information detected by the motion sensor 13 is information regarding an acceleration and an angular velocity.

The control unit 14 includes a microcomputer having a central processing unit (CPU), a read only memory (ROM), a random access memory (RAM), or the like, and executes processing in accordance with a program stored in the ROM to perform overall control of the evaluation device 1.

For example, the control unit 14 performs data communication with the vehicle 2 via the first communication unit 16.

The first communication unit 16 performs short-range wireless communication by a predetermined communication method such as Bluetooth (registered trademark).

Note that communication between the evaluation device 1 and the vehicle 2 is not limited to wireless communication, and may be wired communication.

Furthermore, the control unit 14 performs data communication with an external device via the second communication unit 17.

The second communication unit 17 can perform data communication via the network 3, and the control unit 14 performs data communication with the external device (the server device 4, especially in the present example) connected to the network 3 via the second communication unit 14.

The control unit 14 performs, on the basis of a user's electroencephalogram detected by the electroencephalogram sensor 11, an evaluation of a state related to sensing of danger by the user, and processing of transmitting information to the vehicle 2 or the server device 4 in accordance with an evaluation result, which will be described later.

The storage unit 15 comprehensively represents storage devices such as a hard disk drive (HDD), a solid state drive (SSD), and the like, and is used for storing various types of data in the evaluation device 1. The storage unit 15 stores various types of data required for control by the control unit 14. In particular, the storage unit 15 of the present example stores an evaluation table 15a used by the control unit 14 to perform the above-described evaluation of a state related to sensing of danger, which will be described later.

1-3. Configuration of Vehicle

Figure 4:
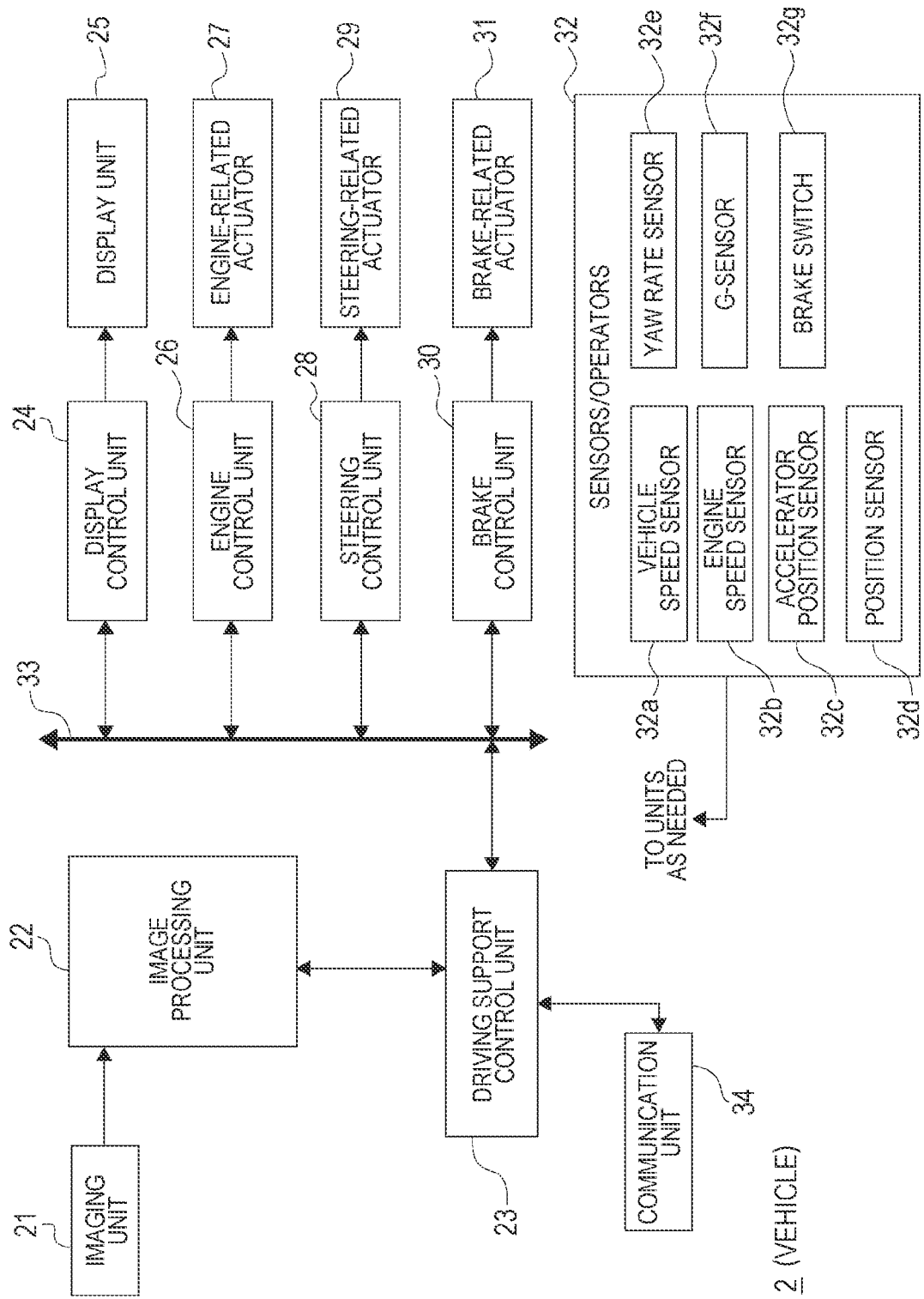
FIG. 4 is a diagram illustrating an internal configuration example of a vehicle as the embodiment.

FIG. 4 is a diagram illustrating an internal configuration example of the vehicle 2.

Note that, in FIG. 4, only a configuration of a main part according to the present technology is mainly extracted from the internal configuration of the vehicle 2 and illustrated.

The vehicle 2 includes an imaging unit 2 that images the outside of the vehicle, an image processing unit 22 that processes an image captured by the imaging unit 2, and a driving support control unit 23 that performs a control related to driving support. The vehicle 2 also includes a display control unit 24, a display unit 25, an engine control unit 26, an engine-related actuator 27, a steering control unit 28, a steering-related actuator 29, a brake control unit 30, a brake-related actuator 31, sensors/operators 32, a bus 33, and a communication unit 34.

The imaging unit 21 has at least two camera units that image the outside of the vehicle. Each camera unit includes a camera optical system and an image sensor such as a charge coupled device (CCD) or a complementary metal oxide semiconductor (CMOS). The camera optical system causes a subject image to be formed as the image on an imaging area of the image sensor, and an electric signal corresponding to an amount of received light is obtained for each pixel.

In the imaging unit 21, the two camera units are pointing in a traveling direction of the vehicle. These two camera units are installed so as to enable distance measurement by a so-called stereo imaging method. An electric signal obtained by each camera unit is subjected to analog-to-digital conversion and predetermined correction processing, and is supplied to the image processing unit 22 as a digital image signal (captured image data) representing a luminance value with a predetermined gradation for each pixel.

The image processing unit 22 includes a microcomputer having, for example, a CPU, a ROM, a RAM, or the like, and executes predetermined image processing related to recognition of an environment outside the vehicle on the basis of captured image data obtained by the imaging unit 21 imaging the outside of the vehicle.

In particular, the image processing unit 22 executes various types of image processing based on each piece of captured image data obtained by stereo imaging, recognizes front information such as data of a three-dimensional object or data of a white line in front of an own car, and estimates a path the own car is traveling on the basis of these pieces of recognized information and the like. Moreover, the image processing unit 22 detects a preceding vehicle on the path the own car is traveling on the basis of the recognized data of a three-dimensional object and the like.

Specifically, the image processing unit 22 performs, for example, the following processing as the processing based on each piece of captured image data obtained by stereo imaging. First, for a pair of captured images as each piece of captured image data, distance information is generated on the basis of the principle of triangulation from a displacement amount (parallax) between corresponding positions. Then, a well-known grouping processing is performed on the distance information, and the distance information after the grouping processing is compared with three-dimensional road shape data, data of a three-dimensional object, and the like stored in advance, and thus data of a white line, data of a side wall such as a guardrail, a curb, or the like that exists along a road, data of a three-dimensional object such as a vehicle, and the like are extracted. Moreover, the image processing unit 22 estimates the path the own car is traveling on the basis of data of a white line, data of a side wall, and the like, and extracts (detects), as another vehicle in the same direction, a three-dimensional object that exists on the path the own car is traveling (including a lane in which the own car is traveling and its adjacent traveling lane in a case of multiple traveling lanes each way) and is moving in substantially the same direction as the own vehicle at a predetermined speed (e.g., 0 Km/h or more). Then, when another vehicle in the same direction has been detected, as information of that vehicle, a relative distance (distance from the own vehicle), a relative speed (rate of change in relative distance), an another vehicle's speed (relative speed+own vehicle's speed), and an another vehicle's acceleration (differential value of the another vehicle's speed) are calculated. Note that the own vehicle's speed is a traveling speed of the own vehicle detected by a vehicle speed sensor 32a described later. The image processing unit 22 recognizes, as a preceding vehicle, another vehicle that exists in the lane in which the own car is traveling, among other vehicles in the same direction. Furthermore, the image processing unit 22 recognizes, as another vehicle in a substantially stopped state, a vehicle that especially has an another vehicle's speed of a predetermined value or less (e.g., 4 Km/h or less) and is not accelerating, among other vehicles in the same direction.

The image processing unit 22 also performs processing of recognizing an object other than other vehicles, such as a pedestrian, an obstacle, or the like, as the above-described data of a three-dimensional object.

The driving support control unit 23 includes a microcomputer having, for example, a CPU, a ROM, a RAM, or the like, and executes various types of control processing related to driving support on the basis of a result of image processing by the image processing unit 22, and detection information and operation input information obtained by the sensors/operators 32, and the like. The driving support control unit 23 is connected via the bus 33 to the display control unit 24, the engine control unit 26, the steering control unit 28, and the brake control unit 30, each of these control units also including a microcomputer, and can mutually perform data communication with each of these control units. The driving support control unit 23 gives an instruction to a control unit as needed among the control units described above to cause the control unit to execute an operation related to the driving support.

The sensors/operators 32 comprehensively represent various sensors and operators provided in the vehicle 2. The sensors/operators 32 include sensors such as the vehicle speed sensor 32a that detects a speed of the own vehicle as an own vehicle's speed, an engine speed sensor 32b that detects an engine speed, an accelerator position sensor 32c that detects an accelerator position, a position sensor 32d that detects a position (positioning) by latitude, longitude, and altitude, a yaw rate sensor 32e that detects a yaw rate, a G-sensor 32f that detects an acceleration, and a brake switch 32g that is turned on or off depending on whether a brake is operated or not.

Furthermore, although not illustrated, the sensors/operators 32 also include other sensors, for example, an intake air amount sensor that detects an amount of air taken into an engine, a throttle position sensor that is interposed in an intake passage and detects a position of a throttle valve that adjusts the amount of intake air supplied to each cylinder of the engine, a water temperature sensor that detects a cooling water temperature that indicates a temperature of the engine, and the like.

Note that, although not illustrated, the sensors/operators 32 include operators for giving various operation instructions to the vehicle 2, for example, an ignition switch for giving an instruction on start/stop of the engine, a turn signal switch for giving an instruction on turning on/off of a turn signal, and the like.

The display unit 25 comprehensively represents display devices installed at positions where they can be visually recognized by the driver. The display control unit 24 controls a display operation by the display unit 25 on the basis of an instruction from a control unit connected to the bus 33, such as the driving support control unit 23 and the like.

The engine control unit 26 controls various actuators provided as the engine-related actuator 27 on the basis of a detection signal from a predetermined sensor in the sensors/operators 32, operation input information by the operators, or the like. As the engine-related actuator 27, various actuators for driving the engine are provided, for example, a throttle actuator that drives the throttle valve and an injector that injects fuel.

For example, the engine control unit 26 controls start/stop of the engine in accordance with an operation of the ignition switch described previously. The engine control unit 26 also controls a fuel injection timing, a fuel injection pulse width, the throttle position, or the like on the basis of a detection signal from a predetermined sensor such as the engine speed sensor 32b or the accelerator position sensor 32c.

The engine control unit 26 can also obtain a desired throttle position from, for example, a map on the basis of an instruction from the driving support control unit 23, and control the throttle actuator (control an engine output) on the basis of the obtained throttle position.

The steering control unit 28 controls an actuator provided as the steering-related actuator 29 on the basis of information regarding a steering angle on which an instruction is given by the driving support control unit 23. The steering-related actuator 29 may be, for example, a steering motor that gives a steering torque to a steering shaft.

With this arrangement, the steering angle can be changed without steering by the driver.

The brake control unit 30 controls various actuators provided as the brake-related actuator 31 on the basis of a detection signal from a predetermined sensor in the sensors/operators 32 or the like. As the brake-related actuator 31, various brake-related actuators are provided, for example, a hydraulic pressure control actuator for controlling an output hydraulic pressure from a brake booster to a master cylinder and a hydraulic pressure in a brake fluid pipe. For example, the brake control unit 30 calculates a slip ratio of a wheel from detection information of a predetermined sensor (e.g., an axle rotation speed sensor or the vehicle speed sensor 32a), and causes the hydraulic pressure control actuator described above to increase or decrease the hydraulic pressure in accordance with the slip ratio to implement so-called antilock brake system (ABS) control.

Furthermore, the brake control unit 30 brakes the vehicle 2 by controlling the above-described hydraulic pressure control actuator on the basis of instruction information regarding the hydraulic pressure output from the driving support control unit 23. This enables so-called automatic braking in which the vehicle 2 is braked without a braking operation by the driver.

The communication unit 34 is connected to the driving support control unit 23. The communication unit 34 performs short-range wireless communication using a communication method similar to that of the first communication unit 16 in the evaluation device 1, such as Bluetooth. This allows the driving support control unit 23 to perform data communication with the control unit 14 in the evaluation device 1.

1-4. Configuration of Server Device

Figure 5:
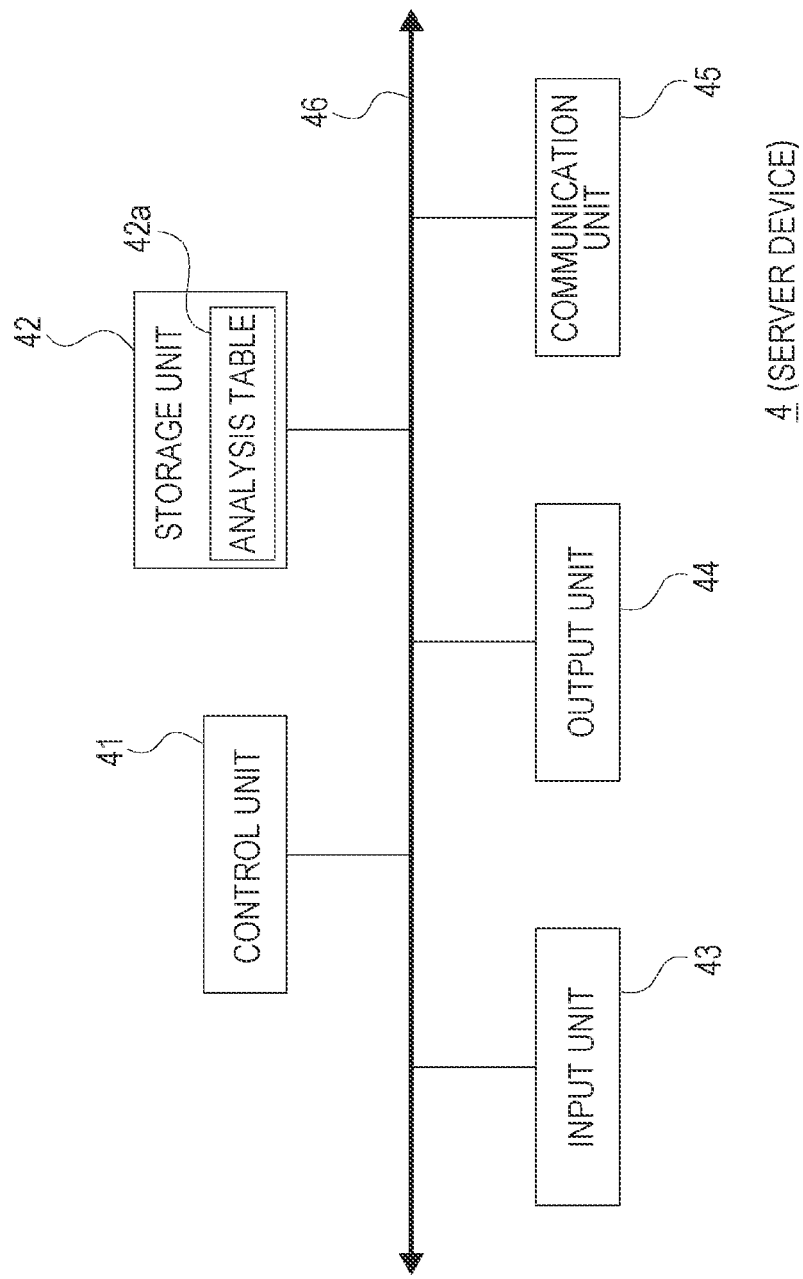
FIG. 5 is a diagram illustrating an internal configuration example of a server device as the embodiment.

FIG. 5 illustrates an internal configuration example of the server device 4.

The server device 4 includes a control unit 41, a storage unit 42, an input unit 43, an output unit 44, a communication unit 45, and a bus 46. As illustrated, the control unit 41, the storage unit 42, the input unit 43, the output unit 44, and the communication unit 45 are connected via the bus 46.

The control unit 41 includes a microcomputer having, for example, a CPU, a ROM, a RAM, or the like, and executes various types of processing in accordance with a program stored in the ROM or a program loaded from the storage unit 42 into the RAM.

The storage unit 42 comprehensively represents storage devices such as an HDD, an SSD, and the like, and is used to store various types of data in the server device 4. For example, the storage unit 42 stores various types of data necessary for control by the control unit 41. Furthermore, the storage unit 42 of the present example especially stores an analysis table 42a created on the basis of acquired information from each evaluation device 1, which will be described later.

The input unit 43 processes an input signal from an input device such as a keyboard, a mouse, or a touch panel, and transmits input information from the input device to the control unit 41.

The output unit 44 includes a display such as a liquid crystal display (LCD) or an organic electroluminescence (EL) panel, a speaker, and the like.

The communication unit 45 can perform data communication with an external device via the network 3. The control unit 41 performs data communication with an external device, especially the evaluation device 1 in the present example, through the network 3 via the communication unit 45.

2. Driving Support Method as Embodiment

Figure 6:
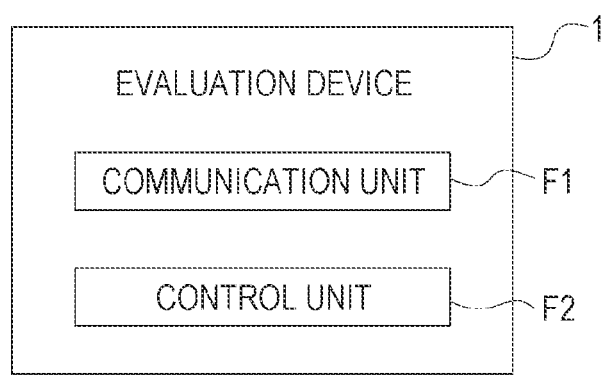
FIG. 6 is a functional block diagram for illustrating functions of the evaluation device as the embodiment.

FIG. 6 is a functional block diagram for illustrating functions of the evaluation device 1.

As illustrated, the evaluation device 1 has functions as a communication unit F1 and a control unit F2.

The communication unit F1 can communicate with the vehicle 2. The function as the communication unit F1 is implemented by the first communication unit 16 in the present example.

The control unit F2 evaluates a state related to sensing of danger by a user on the basis of an electroencephalogram of the user detected by the electroencephalogram sensor 11, and causes the communication unit F1 to transmit evaluation result information to the vehicle 2. The function as the control unit F2 is implemented by the control unit 14 in the present example.

Specifically, the control unit F2 evaluates a state related to sensing of danger on the basis of a beta wave in the electroencephalogram.

Here, the electroencephalogram includes a plurality of components such as a delta wave, a theta wave, an alpha wave, and the beta wave. Each of these components has a different frequency band. For example, the alpha wave is a band component of about 8 Hz to 12 Hz, and the beta wave is a band component of about 13 Hz to 20 Hz. The delta wave is the lowest band component among the delta wave, the theta wave, the alpha wave, and the beta wave. The theta wave is a component of a frequency band between the delta wave and the alpha wave.

Among the components constituting the electroencephalogram, the alpha wave tends to appear in a relaxed state, while the beta wave tends to appear in a tense state. For this reason, in the present example, an evaluation as to whether or not a user has sensed a danger, that is, a determination as to whether the user has sensed a danger is made on the basis of the beta wave.

Specifically, a method of determining whether a danger has been sensed based on the beta wave may be a method based on at least one of a magnitude of amplitude of the beta wave, a power level of the beta wave, or a phase of the beta wave. In the following description, a case of adopting a determination method based on the magnitude of amplitude of the beta wave is exemplified as an example.

Although a determination of whether the user has sensed a danger can be made on the basis of the beta wave alone, in the present example, in order to improve an accuracy of evaluation of whether a danger has been sensed, whether a danger has been sensed is determined on the basis of a relative comparison with another component of the electroencephalogram. Specifically, in the present example, whether or not an amplitude difference $\Delta$ between the alpha wave and the beta wave exceeds a predetermined threshold value TH$\Delta$ is determined as the determination of whether a user has sensed a danger. That is, when the amplitude difference $\Delta$ exceeds the threshold value TH$\Delta$, a determination result "a danger has been sensed" is obtained, and when the amplitude difference $\Delta$ is equal to or less than the threshold value TH$\Delta$, a determination result "a danger has not been sensed" is obtained.

Note that the determination of whether a danger has been sensed is not limited to a determination based on a relative comparison between the beta wave and a single component other than the beta wave as in the above example. The determination can also be made on the basis of a relative comparison between the beta wave and a plurality of components other than the beta wave.

Here, when the determination of whether a user has sensed a danger is made by using the above-described determination method based on the power level of the beta wave, such a method may be performed, as in the above description, on the basis of a result of comparison with a predetermined threshold value.

Furthermore, the determination method based on the phase of the beta wave is a method for a case where an electroencephalogram is detected at a plurality of positions of the brain by a plurality of electrodes. A method of evaluating whether a danger has been sensed on the basis of beta waves at a plurality of positions may be a method in which an arithmetic mean of the beta waves at the plurality of positions is used as an evaluation index of whether a danger has been sensed. In this case, if the beta waves differ in phase depending on the position, there is a possibility that the evaluation index may not be accurately calculated because waveforms may cancel each other at least between some of the beta waves when the beta waves at the corresponding positions are added for calculation of the above-described evaluation index. For this reason, a phase component is extracted from the beta wave at each position by Fourier transform, and how the phase component changes within a specific time range is analyzed and reflected in the calculation of the evaluation index. This makes it possible to improve the accuracy of evaluation of whether a danger has been sensed.

As a result of a determination of whether a danger has been sensed as described above, if it is determined that a danger has been sensed, the control unit F2 of the present example causes the communication unit F1 to transmit, to the vehicle 2 (the driving support control unit 23), information indicating a result of evaluation of a state related to sensing of danger, that is, evaluation result information.

With this arrangement, on the vehicle 2 side, it is possible to start, before the user takes an avoidance behavior for avoiding danger such as sudden braking or sudden steering in accordance with sensing of danger, a driving support control for danger avoidance. For example, a control for braking or steering of the vehicle 2 can be started.

There is a fair time lag from when a person senses a danger to when the person takes an avoidance behavior, because a command transmission to a motor area in the brain and a command transmission from the motor area to a muscle as needed are required. On the other hand, it takes a very short time to evaluate whether a danger has been sensed from an electroencephalogram detection result and transmit evaluation result information, and it takes a very short time for the vehicle 2 side to start a driving support control on the basis of the evaluation result information. This makes it possible to start a driving support control for danger avoidance before the user senses a danger and actually takes a behavior.

Note that, as an evaluation of a state related to sensing of danger by a user, the control unit F2 of the present example performs, besides a determination of whether a danger has been sensed based on a detected electroencephalogram as described above, an evaluation using the evaluation table 15a (see FIG. 3) described previously, and this evaluation will be described later.

Here, when the electroencephalogram sensor 11 detects an electroencephalogram, noise in the electroencephalogram occurs when a user's body moves, so noise suppression processing may be performed on an electroencephalogram detection signal on the basis of motion information detected by the motion sensor 13.

Furthermore, as a result of a determination of whether a danger has been sensed as described above, if it is determined that a danger has been sensed, the control unit F2 of the present example performs processing of transmitting, to the server device 4, predetermined information including information regarding the electroencephalogram detected by the electroencephalogram sensor 11.

The information transmitted to the server device 4 here is information provided to the analysis table 42a described previously. Specifically, position information detected by the position sensor 12, motion information detected by the motion sensor 13 (information regarding an acceleration and an angular velocity in the present example), and vehicle information acquired from the vehicle 2 are transmitted together with the information regarding the electroencephalogram detected by the electroencephalogram sensor 11.

At this time, as for the information regarding the electroencephalogram, waveform information of a certain period in the past from a timing of determination that a danger has been sensed is transmitted.

At this time, as the electroencephalogram information, not a signal (electroencephalogram signal) itself detected by the electroencephalogram sensor 11 is transmitted, but a feature amount is extracted from the electroencephalogram signal and information regarding the extracted feature amount is transmitted. Specifically, information regarding the beta wave extracted from the electroencephalogram signal is transmitted.

This makes it possible to reduce the amount of data transmitted to the server device 4.

Furthermore, as for the position information, position information detected by the position sensor 12 is transmitted at the timing of determination that a danger has been sensed.

As for the motion information, information of a certain period from the timing of determination that a danger has been sensed is transmitted. This allows the server device 4 side to analyze an avoidance behavior taken after a danger has been sensed and analyze whether the vehicle 2 has collided or not.

Moreover, as for the vehicle information, information regarding a vehicle speed acquired from the vehicle 2 (driving support control unit 23), and information regarding recognized pedestrians and other cars (information indicating the number of pedestrians recognized, the number of other cars recognized, a positional relationship with the vehicle 2, and the like) are transmitted.

Figure 7:
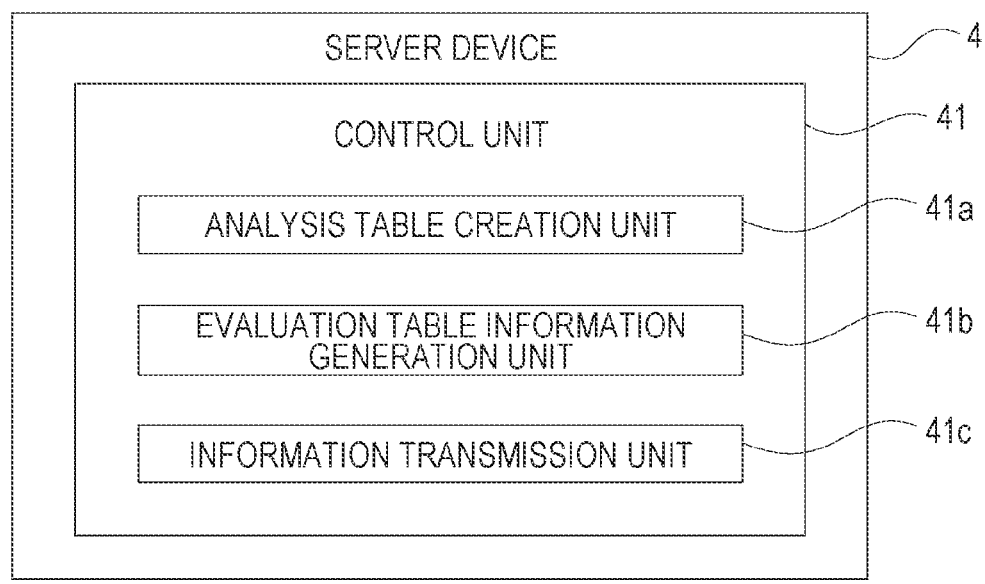
FIG. 7 is a functional block diagram for illustrating functions of the server device as the embodiment.

FIG. 7 is a functional block diagram for illustrating functions of the control unit 41 of the server device 4.

As illustrated, the control unit 41 of the server device 4 has functions as an analysis table creation unit 41a, an evaluation table information generation unit 41b, and an information transmission unit 41c.

The analysis table creation unit 41a creates the analysis table 42a on the basis of electroencephalogram information, position information, motion information, and vehicle information transmitted from the evaluation device 1.

FIG. 8 illustrates an example of a data structure of the analysis table 42a.

As illustrated, in the analysis table 42a, pieces of information regarding a position, electroencephalogram data, an avoidance behavior, a vehicle state, and "collided or not" are associated with each other for each date and time.

The date and time is a date and time when electroencephalogram information, position information, motion information, and vehicle information are received from the evaluation device 1. In the present example, the electroencephalogram information, the position information, the motion information, and the vehicle information are transmitted from the evaluation device 1 in response to a determination that the user has sensed a danger as described above, and it can also be said that the date and time information is information indicating the date and time at which the user has sensed the danger.

The position is position information received from the evaluation device 1, and the electroencephalogram data is electroencephalogram information data received from the evaluation device 1.

The avoidance behavior means an avoidance behavior taken by the user in accordance with sensing of danger, and is analyzed by the control unit 41 on the basis of the motion information received from the evaluation device 1, for example. In the present example, sudden braking and sudden steering are analyzed as an avoidance behavior. Specifically, which of "sudden braking", "sudden steering", or "sudden braking and steering" has been performed as an avoidance behavior is analyzed on the basis of the motion information.

Note that a result that none of these avoidance behaviors has been taken may be obtained from the analysis. In the figure, a blank column in "AVOIDANCE BEHAVIOR" means that no avoidance behavior has been taken.

As the vehicle state, information based on the vehicle information received from the evaluation device 1 is stored. Specifically, in the present example, information indicating a vehicle speed, whether there is a pedestrian, and whether there is another car is stored.

The "collided or not" is information indicating whether the vehicle 2 has collided or not after a danger has been sensed, and is analyzed by the control unit 41 on the basis of the motion information received from the evaluation device 1, for example.

Creating such an analysis table 42a makes it easier to manage a place where a danger has been sensed by a user of the corresponding vehicle 2, an avoidance behavior has been taken, or an accident has occurred, and the analysis table 42a is useful for risk analysis.

Furthermore, in the present example, the analysis table 42a also stores vehicle information (information indicating a vehicle state) at the time of sensing of danger. This enables more detailed risk analysis, for example, more detailed case classification in accordance with a difference in vehicle state when the same avoidance behavior has been taken.

The description returns to FIG. 7.

The evaluation table information generation unit 41b generates, on the basis of information in the analysis table 42a, evaluation table information, which is information to be stored in the evaluation table 15a in the evaluation device 1.

FIG. 9 illustrates an example of a data structure of the evaluation table 15a.

As illustrated, in the evaluation table 15a, pieces of representative electroencephalogram data are associated with the corresponding positions.

The positions here indicate POSITION in the analysis table 42a, that is, positions where a user has sensed a danger in the present example. The representative electroencephalogram data means representative data of electroencephalogram data for each position. In the present example, as representative data, electroencephalogram data calculated as an average waveform of an electroencephalogram (beta wave) for each position is used.

Note that the representative electroencephalogram data is not limited to data obtained by calculating an average waveform. For example, one piece of electroencephalogram data having an average waveform among pieces of electroencephalogram data for each position may be used. It is only required to use representative data of pieces of electroencephalogram data acquired for the position.

The evaluation table information generation unit 41b illustrated in FIG. 7 obtains representative electroencephalogram data of pieces of electroencephalogram data in which positions match, among electroencephalogram data stored in the analysis table 42a.

Note that, as for a position in the analysis table 42a where only one piece of electroencephalogram data has been acquired, the acquired one piece of electroencephalogram data is used as representative electroencephalogram data.

Then, the evaluation table information generation unit 41b generates, as evaluation table information, information in which a position and representative electroencephalogram data are associated with each other.

The information transmission unit 41c performs processing for transmitting the evaluation table information generated by the evaluation table information generation unit 41b to the evaluation device 1. For example, the information transmission unit 41c performs processing of transmitting the evaluation table information in response to a request from the evaluation device 1.

The evaluation device 1 that has requested evaluation table information generates the evaluation table 15a as illustrated in FIG. 9 on the basis of the received evaluation table information. Alternatively, when the evaluation table 15a has already been generated on the basis of evaluation table information received in the past, an information content of the evaluation table 15a is updated on the basis of the received evaluation table information. With this arrangement, the information content of the evaluation table 15a can be updated to the latest content.

Here, in the evaluation device 1 of the present example, the control unit F2 performs, as an evaluation of a state related to sensing of danger by a user, not only an evaluation of whether a danger has been sensed based on the magnitude of amplitude of the beta wave as described above, but also an evaluation based on the evaluation table 15a.

Specifically, in response to a determination that a user has sensed a danger based on the magnitude of amplitude of the beta wave, the control unit F2 acquires, from the evaluation table 15a, representative electroencephalogram data corresponding to a current position detected by the position sensor 12. At this time, the representative electroencephalogram data corresponding to the current position may include not only representative electroencephalogram data associated with a position that matches the current position among the positions in the evaluation table 15a, but also representative electroencephalogram data associated with a position in which an error with respect to the current position is within a predetermined error, for example, several meters to about a dozen meters.

Then, the control unit F2 determines whether or not the acquired representative electroencephalogram data and electroencephalogram data acquired from the electroencephalogram sensor 11 (electroencephalogram data used for the evaluation of whether a danger has been sensed) match. If it is determined that the two pieces of data match, high-level alert information is generated as alert information for the vehicle 2, and is transmitted to the vehicle 2 side by the first communication unit 16.

With this arrangement, when it is evaluated that the user has sensed a danger on the basis of the magnitude of amplitude of the beta wave, and the electroencephalogram at that time matches the electroencephalogram detected at the time of sensing of danger at the current position in the past, that is, when it is evaluated that a certainty that the user has sensed a danger is higher, high-level alert information is transmitted as alert information for the vehicle 2.

On the other hand, when the control unit F2 determines that the representative electroencephalogram data acquired from the evaluation table 15a and the electroencephalogram data acquired from the electroencephalogram sensor 11 do not match, or the evaluation table 15a does not contain representative electroencephalogram data corresponding to the current position, low-level alert information is generated as alert information for the vehicle 2, and is transmitted to the vehicle 2 side by the first communication unit 16. That is, if it is evaluated that the certainty that the user has sensed a danger is relatively low, low-level alert information is transmitted.

Here, in the vehicle 2 of the present example, the driving support control unit 23 enables step-by-step switching of a level of driving support control, for example, an allowable level for sudden braking or sudden steering (how much "sudden" braking or steering is allowed). Then, when the alert information received from the evaluation device 1 is low-level alert information, the driving support control unit 23 performs a driving support control in which the allowable level for sudden braking or sudden steering is "normal". On the other hand, when the alert information received from the evaluation device 1 is high-level alert information, a driving support control is performed with the allowable level for sudden braking or sudden steering raised to a level higher than "normal" (that is, a state in which a driving support control with an enhanced danger avoidance ability can be performed).

As described above, the evaluation device 1 evaluates a state related to sensing of danger by a user, including not only the magnitude of amplitude of the beta wave but also match/mismatch with the representative electroencephalogram data in the evaluation table 15a, and transmits alert information in accordance with the evaluation level to the vehicle 2 side, so that the level of driving support control can be switched on the vehicle 2 side in accordance with the evaluation level for the state related to sensing of danger by the user.

This allows a driving support control to be executed with an appropriate control level. For example, it is possible to prevent a driving support control from being executed with an excessive control level when the certainty that the user has sensed a danger is low.

3. Processing Procedure

With reference to a flowchart in FIG. 10, a processing procedure to be executed by the evaluation device 1 for implementation of a driving support method as the embodiment described above will be described.

Figure 10:
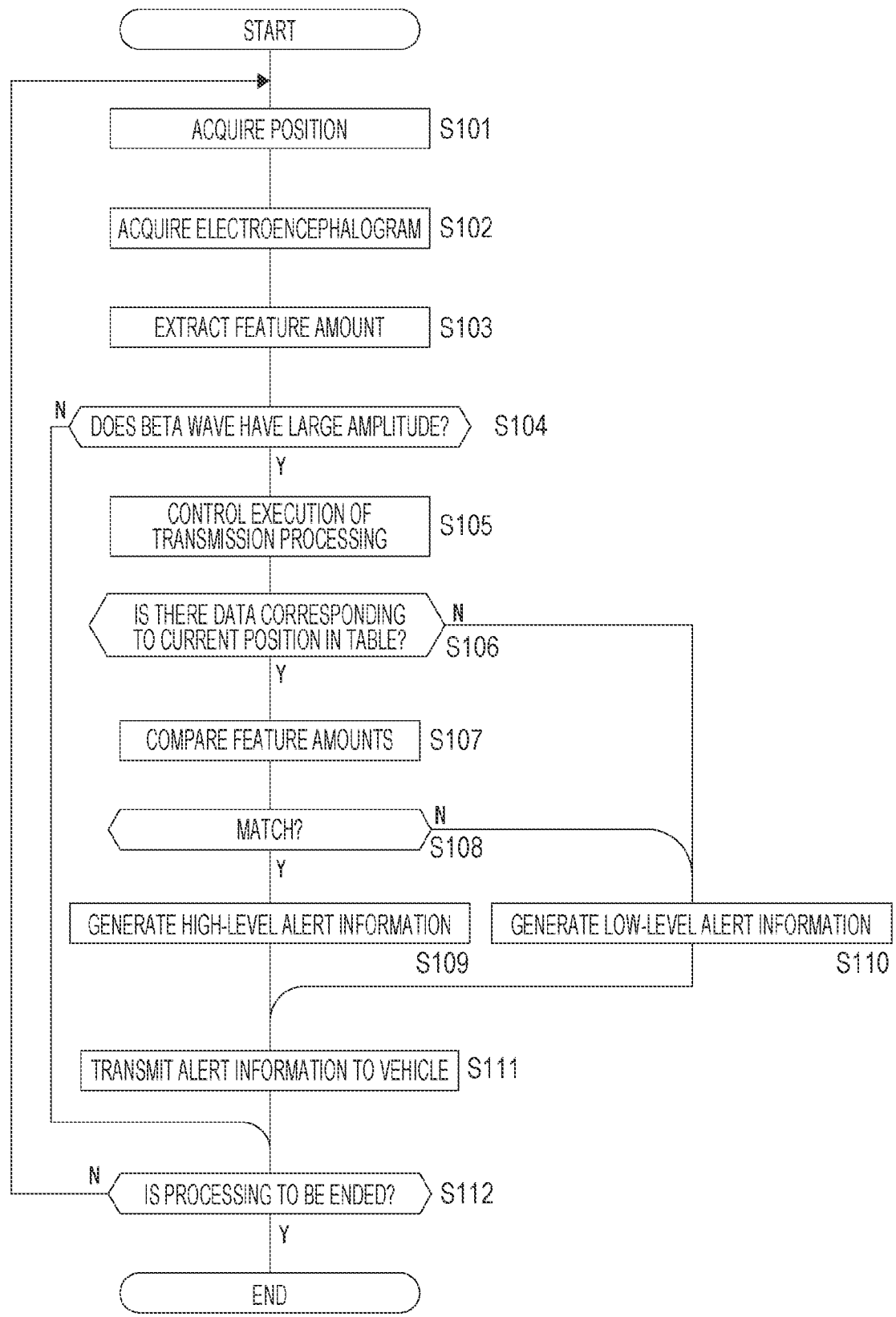
FIG. 10 is a flowchart illustrating a processing procedure to be executed by the evaluation device in order to implement a driving support method as the embodiment.

Note that the processing illustrated in FIG. 10 is executed by the control unit 14 in the evaluation device 1 in accordance with a program stored in the ROM.

In FIG. 10, the control unit 14 first performs processing of acquiring position information (current position information) detected by the position sensor 12 as position acquisition processing of step S101.

Next, in step S102, the control unit 14 acquires an electroencephalogram detected by the electroencephalogram sensor 11 as electroencephalogram acquisition processing, and then performs feature amount extraction processing of step S103 to perform processing of extracting beta wave and alpha wave components from the acquired electroencephalogram.

In step S104 following step S103, the control unit 14 determines whether or not the beta wave has a large amplitude. That is, in the present example, an amplitude difference $\Delta$ between the beta wave and the alpha wave obtained in step S103 is calculated, and it is determined whether or not the amplitude difference $\Delta$ exceeds a threshold value TH$\Delta$.

If the amplitude difference $\Delta$ does not exceed the threshold value TH$\Delta$ and a negative result that the amplitude of the beta wave is not large is obtained, the control unit 14 proceeds to step S112 and determines whether or not the processing is to be ended, that is, for example, whether or not a predetermined condition for ending the processing such as the evaluation device 1 being powered off is satisfied is determined. If the processing is not to be ended, the processing returns to step S101. That is, if it is determined that the amplitude of the beta wave is not large, transmission of information to the server device 4 (S105) and transmission of alert information to the vehicle 2 (S111) are not performed.

On the other hand, if the amplitude difference $\Delta$ exceeds the threshold value TH$\Delta$ and a positive result that the amplitude of the beta wave is large is obtained, the control unit 14 proceeds to step S105, and controls execution of processing of transmitting information to the server device 4 as transmission processing execution control.

Here, the processing of transmitting information to the server device 4 will be described with reference to a flowchart in FIG. 11. In the present example, the control unit 14 can execute the transmission processing illustrated in FIG. 11 in parallel with the processing illustrated in FIG. 10. The control unit 14 starts the transmission processing illustrated in FIG. 11 in accordance with the execution control in step S105.

Figures 11, 12:
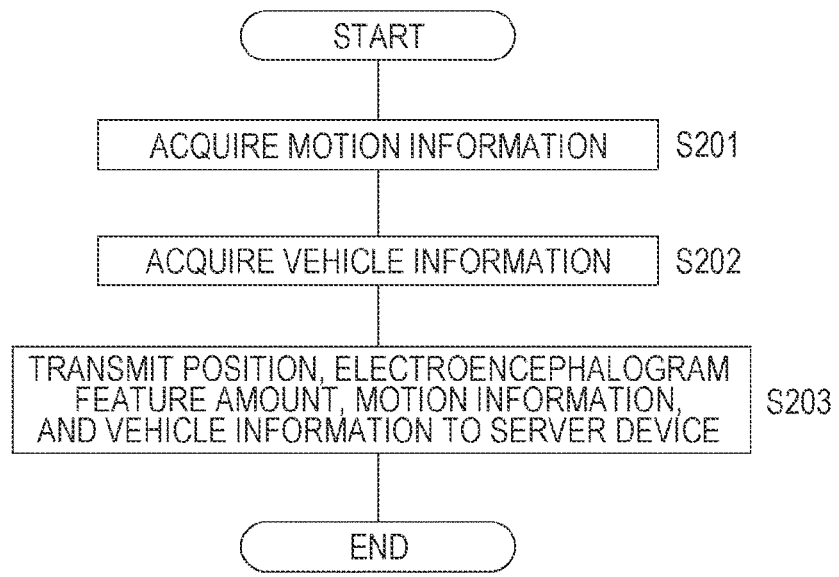
FIG. 11 is a flowchart of processing of transmitting information to the server device executed by the evaluation device as the embodiment.
FIG. 12 illustrates an example of a data structure of an evaluation table in a first modification.

In FIG. 11, the control unit 14 executes processing of acquiring motion information in step S201. That is, motion information detected by the motion sensor 13 is acquired. As will be understood from the above description, as the motion information here, information for a certain period from a timing of determination that a danger has been sensed (that is, a timing of acquisition of the positive result in step S104) is acquired.

Next, in step S202, the control unit 14 executes processing of acquiring vehicle information from the vehicle 2 as vehicle information acquisition processing. As will be understood from the above description, as for the vehicle information, information regarding the vehicle speed and information regarding recognition of pedestrians and other cars are acquired from the driving support control unit 23.

Then, in the following step S203, the control unit 14 executes processing for transmitting the position, the electroencephalogram feature amount, the motion information, and the vehicle information to the server device 4. That is, the current position information acquired in step S101, the feature amount as the beta wave extracted in step S103, and the motion information and the vehicle information respectively acquired in steps S201 and S202 are transmitted to the server device 4 by the second communication unit 17.

The description returns to FIG. 10.

After having executed the transmission processing execution control in step S105, the control unit 14 determines in step S106 whether or not there is data corresponding to the current position in a table. That is, it is determined whether or not representative electroencephalogram data corresponding to the current position exists in the evaluation table 15a.

If there is data corresponding to the current position in the table, the control unit 14 proceeds to step S107 and executes feature amount comparison processing. That is, matching is performed between data of the beta wave extracted in step S103 and the representative electroencephalogram data (beta wave in the present example) corresponding to the current position that has been confirmed in step S106 to exist in the evaluation table 15a.

Then, in the following step S107, the control unit 14 determines whether or not the two pieces of data match as a result of the matching.

If it is determined that the two pieces of data match, the control unit 14 proceeds to step S109, generates high-level alert information, and then executes processing for transmitting the alert information to the vehicle 2 in step S111. That is, the generated alert information is transmitted to the vehicle 2 side via the first communication unit 16.

Furthermore, if it is determined in step S106 that there is no data corresponding to the current position in the table, or if it is determined in step S108 that the pieces of data do not match, the control unit 14 proceeds to step S110 and generates low-level alert information in either case. Then, after having executed the processing of step S110, the control unit 14 executes alert information transmission processing of step S111.

With this arrangement, when the detected electroencephalogram does not match an electroencephalogram acquired at the same position in the past, or when it is impossible to determine whether the detected electroencephalogram matches an electroencephalogram in the past because there is no electroencephalogram data corresponding to the evaluation table 15a in the first place, low-level alert information is transmitted to the vehicle 2.

After having executed the transmission processing of step S111, the control unit 14 executes the end determination processing of step S112 described above.

If it is determined in step S112 that the processing is to be ended, the control unit 14 ends the series of processing illustrated in FIG. 10.

4. Modifications of Embodiment 4-1. First Modification

Here, the server device 4 can analyze a recommended avoidance behavior for avoiding an accident for each position on the basis of the analysis table 42a as illustrated in FIG. 8. The recommended avoidance behavior can be obtained, for example, by analyzing, for each position, an avoidance behavior in which a rate of "COLLIDED OR NOT" in the analysis table 42a being "NOT COLLIDED" is a predetermined value or more.

In the present modification, the recommended avoidance behavior is also analyzed for each vehicle state. That is, there may be cases in which the recommended avoidance behavior differs depending on the vehicle state, for example, when the vehicle 2 is traveling at a low speed, performing sudden braking as an avoidance behavior results in a relatively significantly low accident rate, and when the vehicle 2 is traveling at a high speed, performing sudden braking and sudden steering as an avoidance behavior results in a relatively significantly low accident rate. Thus, in the analysis of the recommended avoidance behavior for each position, a relationship between an avoidance behavior and an accident rate is analyzed for each vehicle state, and when the avoidance behavior with a low accident rate differs relatively significantly depending on the vehicle state, the different avoidance behaviors are assigned as recommended avoidance behaviors for the corresponding vehicle states at the position. On the other hand, in a case of a position where the avoidance behavior with a low accident rate is narrowed down to a single avoidance behavior regardless of the vehicle state, the single avoidance behavior is assigned as the recommended avoidance behavior for the position. Furthermore, depending on the position, there may be a case where no significant difference occurs in the accident rate whichever avoidance behavior is taken. In such a case, assignment as the recommended avoidance behavior for the position is not performed.

In the server device 4 in the present modification, the control unit 41 performs processing of obtaining representative electroencephalogram data for each position described previously on the basis of the analysis table 42a, and also performs processing of analyzing the recommended avoidance behavior for each position as described above. Then, evaluation table information is generated on the basis of results of those pieces of processing. Specifically, as the evaluation table information in this case, when a position, representative electroencephalogram data, and a recommended avoidance behavior for the position are included, the information is generated in association with the recommended avoidance behavior.

FIG. 12 illustrates an example of a data structure of an evaluation table 15a in the present modification. In the example described here, as an analysis of a recommended avoidance behavior for each vehicle state, avoidance behaviors at low speed and avoidance behaviors at high speed are separately analyzed.

In a case of a position where the avoidance behavior with a low accident rate at a low speed (e.g., less than 40 km/h) and that at a high speed (e.g., 40 km/h or more) are relatively significantly different, the control unit 41 in the server device 4 generates evaluation table information in which each of the avoidance behavior at low speed and the avoidance behavior at high speed is assigned as a recommended avoidance behavior.

Furthermore, in a case of a position where the avoidance behavior with a low accident rate is narrowed down to a single avoidance behavior regardless of at low speed or at high speed, the control unit 41 generates evaluation table information in which the single avoidance behavior is assigned as the recommended avoidance behavior. In a case of a position where no significant difference occurs in the accident rate regardless of at low speed or at high speed whichever avoidance behavior is taken, the control unit 41 generates evaluation table information in which only the representative electroencephalogram data is associated.

In this case, the control unit 14 in the evaluation device 1 requests the server device 4 to transmit evaluation table information. Then, the evaluation table 15a is generated or updated on the basis of the evaluation table information received in response to the request. With this arrangement, the evaluation table 15a as illustrated in FIG. 12 is built in the storage unit 15 in this case.

The control unit 14 in the present modification causes information regarding the recommended avoidance behavior to be transmitted to the vehicle 2 together with alert information on the basis of the evaluation table 15a illustrated in FIG. 12.

With this arrangement, the vehicle 2 can perform a driving support control on the basis of information indicating the recommended avoidance behavior, that is, an avoidance behavior in which the accident rate has been low in the past with respect to a danger that occurs at the current position, and it is therefore possible to enhance safety. In particular, in the present modification, it is possible to notify the vehicle 2 side of the information regarding the recommended avoidance behavior in accordance with the vehicle state, that is, a driving support control can be performed on the vehicle 2 side on the basis of information indicating an appropriate recommended avoidance behavior in accordance with the vehicle state, and it is therefore possible to further enhance safety.

Figure 13:
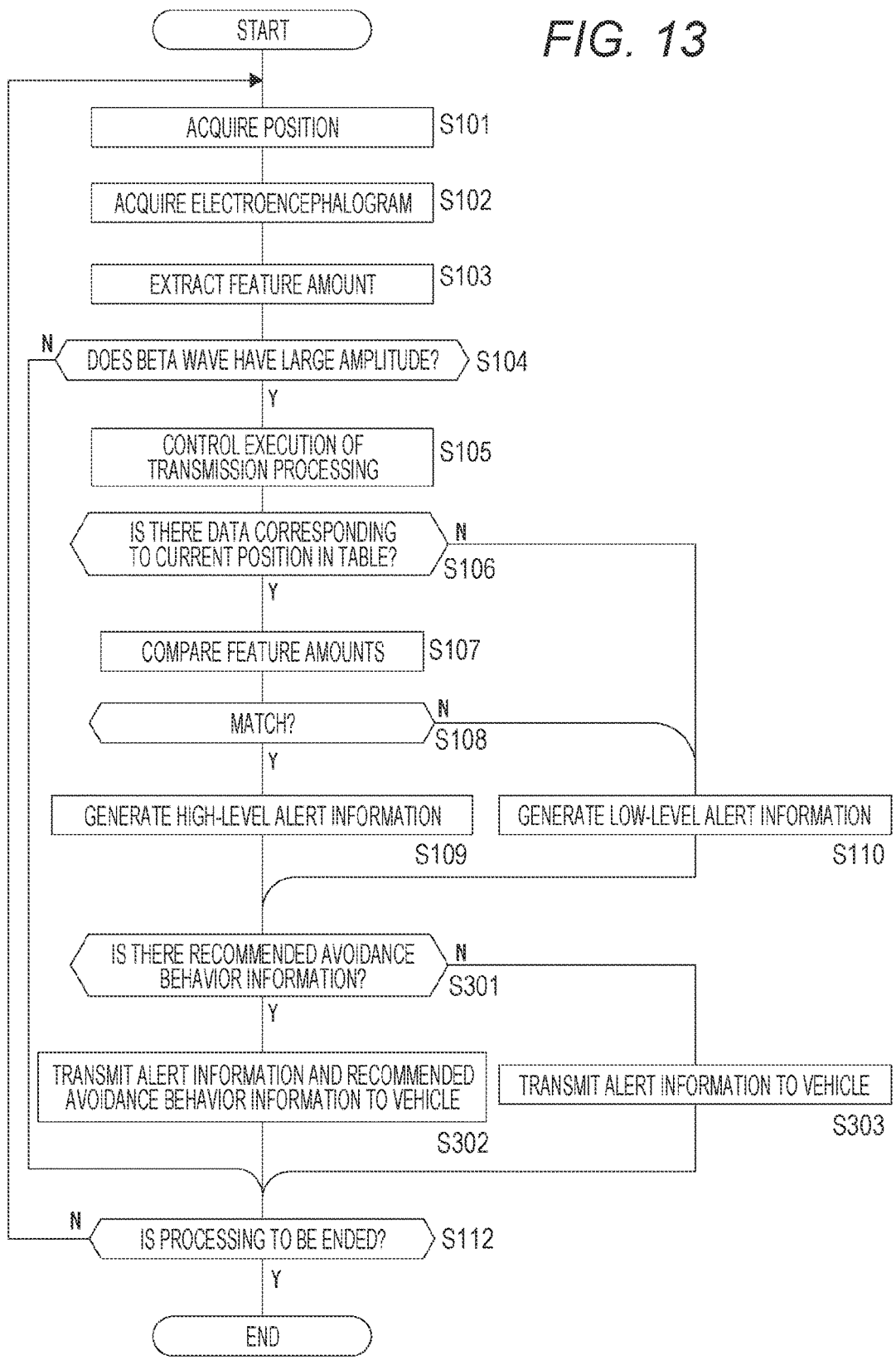
FIG. 13 is a flowchart illustrating a processing procedure to be executed by the evaluation device for implementation of a driving support method as the first modification.

FIG. 13 is a flowchart illustrating a processing procedure to be executed by the control unit 14 of the evaluation device 1 for implementation of the driving support method as a first modification described above.

Note that, in FIG. 13, the same step number is given to processing similar to the processing already described in FIG. 10, and the description thereof will be omitted.

In this case, the control unit 14 executes the processing of steps S301 to S303 instead of the processing of step S111.

Specifically, in this case, if the control unit 14 has generated high-level alert information in step S109, or if the control unit 14 has generated low-level alert information in step S110, the processing proceeds to step S301 in either case.

In step S301, the control unit 14 determines whether or not a recommended avoidance behavior corresponding to the current position exists in the evaluation table 15*a*. If it is determined that a recommended avoidance behavior exists, the control unit 14 executes processing for transmitting alert information and recommended avoidance behavior information to the vehicle 2 in step S302, and the processing proceeds to step S112.

On the other hand, if it is determined that no recommended avoidance behavior exists, the control unit 14 executes processing for transmitting alert information to the vehicle 2 in step S303, and the processing proceeds to step S112.

4-2. Second Modification

Here, in the embodiment, if it is determined that a user has sensed a danger on the basis of the beta wave, a state related to sensing of danger is evaluated on the basis of a result of matching with representative electroencephalogram data corresponding to the current position. The representative electroencephalogram data in this case may be representative electroencephalogram data at the time of an avoidance behavior.

In this case, the evaluation table 15*a* stores, as the representative electroencephalogram data, representative electroencephalogram data regarding a case where a user has sensed a danger and then taken an avoidance behavior. That is, the control unit 14 in this case performs matching between representative electroencephalogram data corresponding to the current position in the evaluation table 15*a* and electroencephalogram data from the electroencephalogram sensor 11 as in the processing of steps S106 to S108, so that matching can be performed with an electroencephalogram immediately before an avoidance behavior taken at the current position in the past. That is, instead of vaguely evaluating whether a danger has been sensed, it is possible to evaluate whether or not a danger of a level that causes an avoidance behavior to be taken has been sensed.

Here, the evaluation operation by the control unit 14 as a second modification as described above can also be said as follows. That is, when the current position is a position where an avoidance behavior has been taken in the past and an electroencephalogram immediately before the avoidance behavior has been recorded, the control unit 14 evaluates a state related to sensing of danger by a user on the basis of a result of matching between an electroencephalogram detected by the electroencephalogram sensor 11 and the electroencephalogram immediately before the avoidance behavior.

This makes it possible to appropriately evaluate, on the basis of past records, a possibility that a user will take an avoidance behavior such as sudden braking or sudden steering in accordance with sensing of danger.

It is therefore possible to cause, when a user is likely to take an avoidance behavior, the vehicle 2 side to start a driving support control for the avoidance behavior, and it is therefore possible to enhance safety.

4-3. Other Modifications

In the above description, it has been described that the analysis table 42*a* in the server device 4 accumulates information regarding electroencephalograms transmitted from each evaluation device 1, but it is possible to accumulate not only electroencephalograms but also biological information other than electroencephalograms, such as an amount of sweat, a heart rate, a pulse rate, or the like collected from each evaluation device 1.

At that time, the evaluation device 1 is provided with a corresponding biosensor, and biological information detected by the biosensor is transmitted to the server device 4.

Furthermore, when an accident occurs, the user does not always sense the danger in advance. Examples of such an accident include an accident caused by inattentive driving and an accident of being rear-ended by another vehicle from behind.

In order to enable identification of such an accident by analysis on the server device 4 side, it is conceivable to transmit motion information from the evaluation device 1 side even when a determination of whether a danger has been sensed based on the beta wave is performed and it is determined that no danger has been sensed. Specifically, it is conceivable to determine, also on the evaluation device 1 side, whether a collision has occurred on the basis of motion information such as an acceleration, and transmit, in response to a determination that a collision has occurred, to the server device 4, information regarding an electroencephalogram immediately before the collision. Alternatively, it is also conceivable to constantly transmit electroencephalogram information to the server device 4.

Furthermore, in the example described above, analysis for generating the analysis table 42*a* based on information transmitted from the evaluation device 1 and analysis for generating evaluation table information based on the analysis table 42*a* are executed by the server device 4 (the control unit 41), but these analyses can also be executed outside the server device 4.

Note that the above description shows an example in which the present technology is applied to a vehicle as a motorcycle, but the present technology can be applied not only to a motorcycle but also to a vehicle with three or more wheels. Furthermore, the present technology is not limited to automobiles, and can also be applied to human-powered vehicles (e.g., a bicycle having a steering support function).

Furthermore, the above description shows an example in which the position sensor 12 and the motion sensor 13 are integrally provided in the evaluation device 1, but a configuration may be adopted in which at least one of these sensors is externally attached to the evaluation device 1.

5. Summary of Embodiment

As described above, an evaluation device (the evaluation device 1) as the embodiment includes a communication unit (the communication unit F1 or the first communication unit 16) capable of communicating with a vehicle, and a control unit (the control unit F2 or 14) that evaluates a state related to sensing of danger by a user on the basis of an electroencephalogram of the user detected by an electroencephalogram sensor and causes the communication unit to transmit evaluation result information to the vehicle.

That is, for example, on the basis of an electroencephalogram of a user such as a driver of a vehicle, evaluation of a state related to sensing of danger such as whether or not the user has sensed a danger is performed, and evaluation result information is transmitted to the vehicle side.

There is a fair time lag from when a person senses a danger to when the person takes an avoidance behavior, because a command transmission to a motor area in the brain and a command transmission from the motor area to a muscle as needed are required. On the other hand, when a danger is sensed, the brain reacts, and this appears as a change in the electroencephalogram. It is therefore possible to obtain evaluation result information related to sensing of danger on the basis of the electroencephalogram and transmit it to the vehicle side as described above to allow the vehicle to start a control for danger avoidance at a stage before the user takes an avoidance behavior in accordance with sensing of danger.

It is therefore possible to enhance safety in vehicle operation.

Furthermore, in the evaluation device as the embodiment, the control unit evaluates a state related to sensing of danger on the basis of at least one of the magnitude of amplitude of the beta wave in the electroencephalogram, the power level of the beta wave, or the phase of the beta wave.

When a danger approaches and tension rises, an amplitude and power of a beta wave change. Furthermore, when beta waves detected at a plurality of positions in a brain are out of phase, there is a possibility that the evaluation of a state related to sensing of danger becomes less accurate. Thus, the state is evaluated in consideration of a magnitude of amplitude, a power level, and a phase of a beta wave.

It is therefore possible to appropriately evaluate a state related to sensing of danger by a user.

Furthermore, it is not necessary to perform matching with an electroencephalogram detected in the past to evaluate sensing of danger. It is therefore possible to appropriately evaluate sensing of danger even at a position where there is no record of an electroencephalogram in the past, and it is therefore possible to enhance safety.

Moreover, in the evaluation device as the embodiment, the control unit evaluates a state related to sensing of danger on the basis of a relative comparison between the beta wave and a component other than the beta wave in the electroencephalogram.

That is, the evaluation of a state related to sensing of danger is performed on the basis of a relative comparison with a component other than the beta wave such as an alpha wave or a theta wave, not on the basis of the beta wave alone.

It is therefore possible to improve the accuracy of the evaluation of a state related to sensing of danger.

Furthermore, in the evaluation device as the embodiment, when a current position is a position where an avoidance behavior has been taken in the past and an electroencephalogram immediately before the avoidance behavior has been recorded, the control unit evaluates a state related to sensing of danger on the basis of a result of matching between an electroencephalogram detected by the electroencephalogram sensor and the electroencephalogram immediately before the avoidance behavior (see the second modification).

This makes it possible to appropriately evaluate, on the basis of past records, a possibility that a user will take an avoidance behavior such as sudden braking or sudden steering in accordance with sensing of danger.

It is therefore possible to cause, when a user is likely to take an avoidance behavior, the vehicle side to start a driving support control for the avoidance behavior, and it is therefore possible to enhance safety.

Furthermore, in the evaluation device as the embodiment, the control unit executes transmission processing for transmitting, to an external device, current position information, information regarding an electroencephalogram detected by the electroencephalogram sensor, and motion information detected by a motion sensor.

This makes it possible to build, outside the evaluation device, a database (table information) for managing information such as a place where a user has sensed a danger, an electroencephalogram at the time of sensing of danger, a content of an avoidance behavior taken in accordance with sensing of danger, and whether an accident has occurred (whether a collision has occurred).

It is therefore possible to facilitate analysis of a dangerous place.

Moreover, in the evaluation device as the embodiment, the control unit executes transmission processing in accordance with a result of an evaluation of a state related to sensing of danger.

This allows processing of transmitting information for risk analysis such as an electroencephalogram to an external device to be executed if it is evaluated that a user has sensed a danger, and not to be executed if it is evaluated that the user has not sensed a danger.

It is therefore no longer necessary to constantly transmit information for risk analysis, and thus an amount of communication data and a processing load can be reduced.

Furthermore, in the evaluation device as the embodiment, the control unit extracts a feature amount of an electroencephalogram detected by the electroencephalogram sensor, and performs the transmission processing to transmit information regarding the extracted feature amount.

With this arrangement, an amount of data can be reduced as compared with a case where an electroencephalogram signal itself detected by the electroencephalogram sensor is transmitted.

It is therefore possible to reduce the amount of communication data.

Furthermore, in the evaluation device as the embodiment, the control unit performs the transmission processing to transmit vehicle information acquired from the vehicle via the communication unit.

This makes it possible to build, outside the evaluation device, a database for managing information indicating a vehicle state corresponding to the time of sensing of danger, in addition to information indicating a place where a user has sensed a danger, an avoidance behavior has been taken, or an accident has occurred.

It is therefore possible to perform more detailed risk analysis.

Moreover, in the evaluation device as the embodiment, the control unit causes the communication unit to transmit, to the vehicle, information regarding an avoidance behavior recorded in association with a current position on the basis of a result of the evaluation of a state related to sensing of danger.

This makes it possible to transmit, to the vehicle, information regarding an avoidance behavior recorded in association with the current position when it is evaluated that a user has sensed a danger.

It is therefore possible to implement a driving support control with enhanced safety in the vehicle. For example, it is possible to notify the vehicle of an avoidance behavior in which the accident rate has been low in the past with respect to a danger that occurs at the current position.

Furthermore, an evaluation method as the embodiment includes evaluating a state related to sensing of danger by a user on the basis of an electroencephalogram of the user detected by an electroencephalogram sensor, and causing a communication unit capable of communicating with a vehicle to transmit evaluation result information to the vehicle.

Such an evaluation method as the embodiment can also obtain an operation and effect similar to those of the evaluation device as the embodiment described above.

Note that the effects described herein are merely illustrative and are not intended to be restrictive, and other effects may be obtained.

6. Present Technology

Note that the present technology can also be configured as described below.

(1)

An evaluation device including:

a communication unit capable of communicating with a vehicle; and a control unit that performs an evaluation of a state related to sensing of danger by a user on the basis of an electroencephalogram of the user detected by an electroencephalogram sensor, and causes the communication unit to transmit evaluation result information to the vehicle.

(2)

The evaluation device according to (1), in which the control unit performs the evaluation of a state related to sensing of danger on the basis of at least one of a magnitude of amplitude of a beta wave in an electroencephalogram, a power level of the beta wave, or a phase of the beta wave.

(3)

The evaluation device according to (1) or (2), in which the control unit performs the evaluation of a state related to sensing of danger on the basis of a relative comparison between a beta wave and a component other than the beta wave in an electroencephalogram.

(4)

The evaluation device according to any one of (1) to (3), in which the control unit performs, when a current position is a position where an avoidance behavior has been taken in the past and an electroencephalogram immediately before the avoidance behavior has been recorded, the evaluation of a state related to sensing of danger on the basis of a result of matching between an electroencephalogram detected by the electroencephalogram sensor and the electroencephalogram immediately before the avoidance behavior.

(5)

The evaluation device according to any one of (1) to (4), in which the control unit executes transmission processing for transmitting, to an external device, current position information, information regarding an electroencephalogram detected by the electroencephalogram sensor, and motion information detected by a motion sensor.

(6)

The evaluation device according to (5), in which the control unit executes the transmission processing in accordance with a result of the evaluation of a state related to sensing of danger.

(7)

The evaluation device according to (5) or (6), in which the control unit extracts a feature amount of an electroencephalogram detected by the electroencephalogram sensor, and performs the transmission processing for transmitting information regarding the extracted feature amount.

(8)

The evaluation device according to any one of (5) to (7), in which the control unit performs the transmission processing for transmitting vehicle information acquired from the vehicle via the communication unit.

(9)

The evaluation device according to any one of (1) to (8), in which the control unit causes the communication unit to transmit, to the vehicle, information regarding an avoidance behavior recorded in association with a current position on the basis of a result of the evaluation of a state related to sensing of danger.

REFERENCE SIGNS LIST

1 Evaluation device
2 Vehicle
4 Server device
5 Driving support system
11 Electroencephalogram sensor
12 Position sensor
13 Motion sensor
14 Control unit
16 First communication unit
23 Driving support control unit
41 Control unit
41a Analysis table creation unit
41b Evaluation table information generation unit
41c Information transmission unit
42a Analysis table
F1 Communication unit
F2 Control unit

The invention claimed is:

1. An evaluation device, comprising:
at least one communication unit configured to communicate with a vehicle; and
a control unit configured to:
perform an evaluation of a state related to sensing of danger by a user of the vehicle, wherein the evaluation of the state is performed based on an electroencephalogram of the user detected by an electroencephalogram sensor; and cause the at least one communication unit to:
- transmit, to the vehicle, result information representing the evaluation of the state, and
- transmit, to an external device different from the vehicle and the evaluation device, information representing a current position of the user, information regarding the electroencephalogram detected by the electroencephalogram sensor, and motion information of the user detected by a motion sensor.

2. The evaluation device according to claim 1, wherein the control unit is further configured to perform the evaluation of the state related to sensing of danger based on at least one of a magnitude of amplitude of a beta wave in the electroencephalogram, a power level of the beta wave, or a phase of the beta wave.

3. The evaluation device according to claim 1, wherein the control unit is further configured to perform the evaluation of the state related to sensing of danger based on a relative comparison between a beta wave and a component other than the beta wave in the electroencephalogram.

4. The evaluation device according to claim 1, wherein the control unit is further configured to:
- record, into a storage unit, the electroencephalogram immediately before an avoidance behavior of the user;
- perform, when the current position is a position where the avoidance behavior has been taken in past, the evaluation of the state related to sensing of danger based on a result of matching between a current electroencephalogram detected by the electroencephalogram sensor and the recorded electroencephalogram.

5. The evaluation device according to claim 1 wherein the control unit is further configured to:
- determine whether an amplitude difference between an alpha wave and a beta wave in the electroencephalogram exceeds a predetermined threshold; and
- cause, based on the determination that the amplitude difference between the alpha wave and the beta wave in the electroencephalogram exceeds the predetermined threshold, the at least one communication unit to transmit the current position information, the electroencephalogram information, and the motion information to the external device.

6. The evaluation device according to claim 1, wherein the control unit is further configured to:
- extract a feature amount of the electroencephalogram; and
- cause the at least one communication unit to transmit information regarding the extracted feature amount.

7. The evaluation device according to claim 1, wherein the control unit is further configured to cause the at least one communication unit to transmit, to the external device, vehicle information acquired from the vehicle along with the current position information, the electroencephalogram information, and the motion information.

8. The evaluation device according to claim 1, wherein the control unit is further configured to:
- determine, in the evaluation of the state related to sensing of danger, whether the user has sensed the danger, and
- cause, based on the determination that the user has sensed the danger, the at least one communication unit to transmit, to the external device, the motion information during a certain period from a timing of the determination that the user has sensed the danger.

9. An evaluation information processing method, comprising:
- acquiring, from an electroencephalogram sensor, electroencephalogram information of a user of a vehicle;
- acquiring, from a position sensor, current position information representing a current position of the user;
- acquiring, from a motion sensor, motion information of the user;
- determining, in an evaluation of state related to sensing of danger by the user, whether the user has sensed the danger based on the electroencephalogram information; and
- controlling, based on the determination that the user has sensed the danger, at least one communication unit to transmit the electroencephalogram information, the current position information, and the motion information to an external device different from the vehicle.

* * * * *